United States Patent [19]

Shorter et al.

[11] Patent Number: 4,461,045
[45] Date of Patent: Jul. 24, 1984

[54] ARTIFICIAL LEG

[75] Inventors: John J. Shorter, East Oakley; Michael W. Brewer, Basingstoke, both of England

[73] Assignee: Chas. A. Blatchford & Sons Ltd., Hampshire, England

[21] Appl. No.: 445,747

[22] Filed: Nov. 30, 1982

[30] Foreign Application Priority Data

Dec. 10, 1981 [GB] United Kingdom ............. 8137207

[51] Int. Cl.³ ............................................. A61F 1/04
[52] U.S. Cl. ............................................. 3/32; 3/30; 3/5
[58] Field of Search ........................... 3/30, 31, 32

[56] References Cited

U.S. PATENT DOCUMENTS 314,726  3/1885  Rowley .................................. 3/32

FOREIGN PATENT DOCUMENTS 2070439A  9/1981  United Kingdom ............. 3/30

Primary Examiner—Richard J. Apley
Assistant Examiner—David J. Isabella
Attorney, Agent, or Firm—Cushman, Darby & Cushman

[57] ABSTRACT

An improved artificial leg has a ball and socket ankle joint (3) connecting a foot (2) to a shin member (1). The ankle joint comprises a two-part socket (5A, 5B) enclosing a part-spherical ball member (4) with an elastic sleeve (6) sandwiched between the socket and the ball member (4) to allow resilient flexion of the foot (2) relative to the shin member (1). In order to provide relatively more resistance to dorsi-flexion than to plantar-flexion, an elastic buffer in the form of a ring (11) is disposed around a coupling shank portion (4A) of the ball member (4) to engage a downwardly extending anterior skirt portion (12) of the socket. In the preferred embodiment of the invention the skirt portion (12) also extends around each side of the ring (11) to provide resistance to medial and lateral flexion.

13 Claims, 4 Drawing Figures

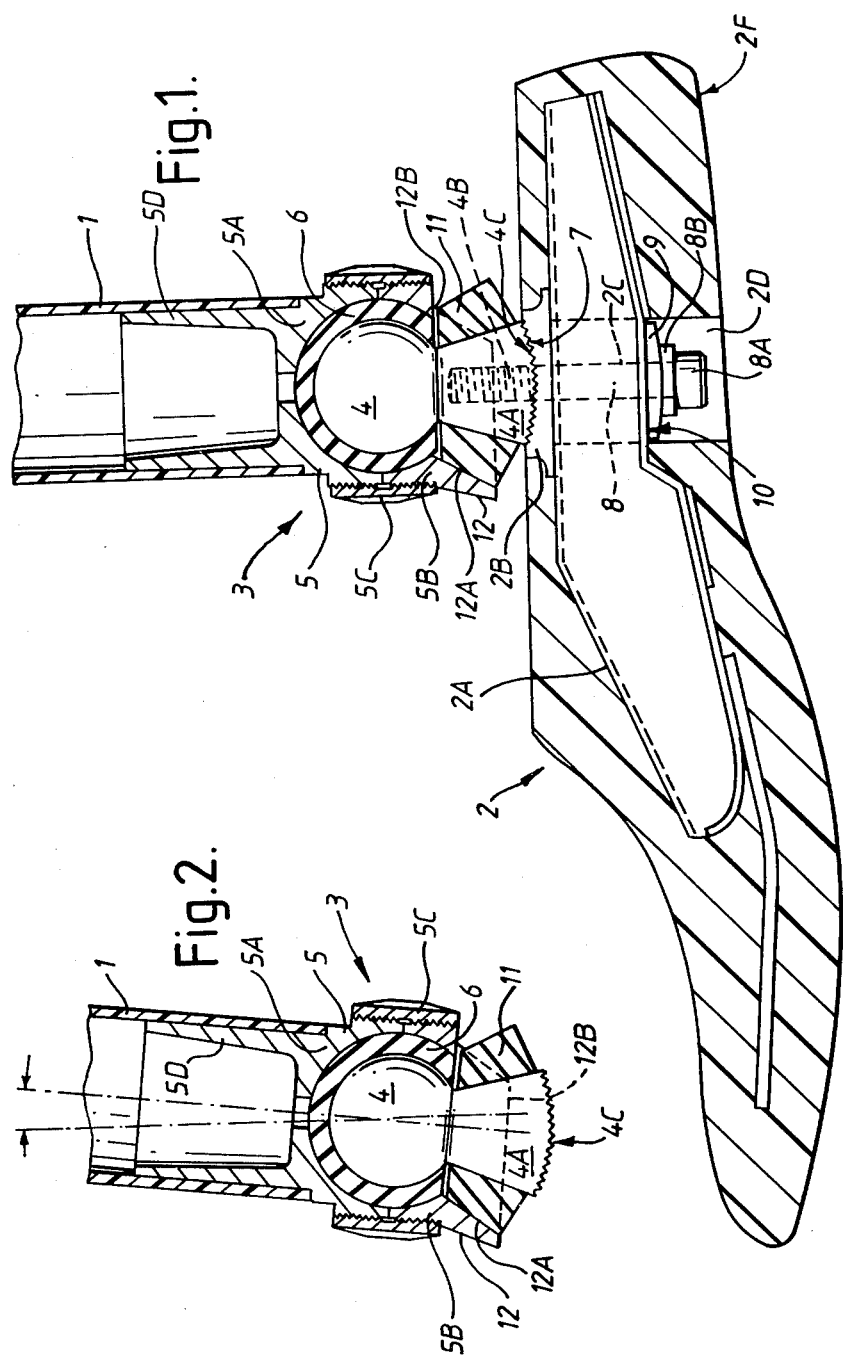

ARTIFICIAL LEG

This invention relates to an artificial leg having a shin member, a foot, and a ball and socket joint connecting the shin member and foot.

It is known, in such an artificial leg, for the ball and socket joint to constitute in effect an ankle; the ball is part-spherical and may be encased in a matching part-spherical cover of rubber or polyurethane or other elastic material over which the socket is fixed. Such an arrangement permits limited cushioned flexion of shin and foot, to give dorsiflexion and plantar-flexion of the foot, and also medial and lateral flexion. "Dorsi-flexion" is upward movement of the fore-part of the foot relative to the shin, whilst "plantar-flexion" is downward movement of the fore-part of the foot relative to the shin. In addition such an arrangement also permits limited relative rotation of the shin relative to the foot about the vertical axis of the shin.

It has been found desirable, in an artificial leg of the kind referred to, to provide relatively greater resistance to dorsi-flexion whilst permitting relatively lower resistance to plantar-flexion. According to one aspect of this invention an artificial leg comprises a shin member and a foot and, connecting the shin member and the foot, a ball and socket joint which includes a socket and a ball member, the ball member having a ball portion within the socket and a coupling shank, wherein the socket includes an extension arranged to co-operate with an elastic buffer mounted between the coupling shank and the extension so as to provide resistance to dorsiflexion of the foot relative to the shin member. The elastic buffer is preferably a thick rubber ring fitting over the ball member shank by which the latter may be fixed to and upstands from, the foot. The extension of the socket preferably partly surrounds the rubber ring and engages it at the front and at the sides, but not at the back.

Also in an artificial leg of the kind referred to, it has been found desirable to provide for adjustment in a simple manner of the angle between the foot and the shin axis. Assuming for example that the shin axis is vertical when the foot is positioned for a normal heel height (for example with the lower surface of the foot at the heel 25 mm above the ground), then, to suit the requirements of a particular patient, it may be desirable to vary that angular relationship between the shin axis and foot. This may be the case for instance if it is required to accommodate a lower or a higher shoe heel.

Thus in a preferred artificial leg in accordance with the invention, the ball member is mounted on the foot in such manner that the ball and the socket member may be adjustably moved about a lateral axis, preferably a horizontal axis passing through the centre of the ball, and then fixed in the adjusted position. In effect this changes the angle of the assembly of the shin member and the ball and socket joint relative to the foot. To achieve this the ball member shank may be provided with a serrated convex lower face which is in adjustable engagement with a correspondingly serrated concave upper face portion of the foot. The serrated faces are preferably arranged to provide the stepwise angular relative adjustment of the shin member and the foot in a substantially vertical plane. The construction is preferably such that the foot may be removed and replaced by another foot if required.

The invention also provides an artificial leg comprising:- a shin member; a foot; a ball and socket joint comprising a ball member attached to the foot and a socket member attached to the shin, the socket member having a downwardly extending anterior stop portion; and an elastic buffer disposed below the joint between the stop portion and the ball member for resisting dorsiflexion of the foot relative to the shin member.

According to a further aspect of the invention an artificial limb component comprises a foot and a ball and socket ankle joint, the ankle joint including a ball member secured to the foot and a socket member for attachment to an upper limb component, wherein the socket member has a downwardly extending anterior stop portion, and wherein an elastic buffer in the form of a ring is disposed between the stop portion and the ball member for resisting dorsi-flexion of the foot relative to the upper limb component.

The invention will now be described by way of example, with reference to the drawings in which:-

FIG. 1 is a central vertical section of an artificial leg in accordance with the invention, taken on an anterior/posterior plane;

FIG. 2 is a detail section of part of the prosthesis of FIG. 1, showing an adjustable position;

Figure 3:
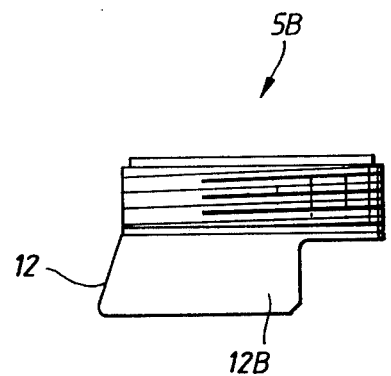
FIG. 3 is a side view of a lower portion of a socket forming part of the ball and socket joint visible in FIG. 1.

Referring to the drawings an artificial leg has a shin tube member 1, a foot 2, and a ball and socket joint 3 which comprises a part-spherical ball portion 4 with an integral depending shank 4A and a socket 5 which comprises upper and lower socket parts 5A, 5B with opposite external threads and a turnbuckle sleeve or locking ring 5C. The upper socket part 5A includes an upward extension 5D over which is fixed the shin tube member 1, as shown. The ball portion 4 is enclosed by a thick rubber part-spherical cover 6, over which are clamped the socket parts 5A, 5B. This ball and socket construction is described more fully in our co-pending British Patent Application No. 81 27383.

The shank 4A has a central vertical threaded bore 4B and a serrated and convexly curved lower face 4C.

The foot 2 has a keel 2A, a mounting plate 2B, a bore 2C and a recess 2D in the sole 2E. The plate 2B has a serrated and concavely curved upper face 7 which matches and mates with the serrated face 4C. In the bores 4B and 2C is a bolt 8 which is threaded into the ball bore 4B and which has its head 8A in engagement with a washer 8B, the upper face of which is concave. A spacer 9 fits against the upper wall 10 of the recess 2D, which upper wall 10 is formed by a part of the keel 2A. The lower face of the spacer 9 is convex, to match the concavity of the upper face of the washer 8B. When the bolt 8 is tightened it draws the shank 4A into engagement with the mounting plate 2B and so fixes the foot to the shin member. In FIG. 1 the shin member is shown with its axis vertical in relation to the foot, the lower heel face 2F of which is 25 mm from the ground.

By slackening off the bolt 8 the assembly of shin and ball and socket joint can be rotated in the anterior/posterior plane about the centre of the ball 4, as indicated by FIG. 2, which shows the shin axis moved 6° in the posterior direction. The serrations on the faces 4C and 7 can be arranged to provide for instance for 2° adjustment steps. It will be understood that if, with such 6° adjustment, the shin is now moved to assume the vertical, the heel height above the ground will have been increased.

In addition the arrangement above described permits removal of the foot, and replacement by another, as disclosed in our co-pending British Patent Application No. 81 06633.

Figure 4:
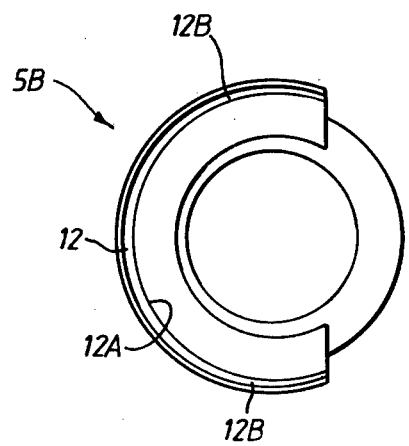
FIG. 4 is an underside view of the socket portion.

With the ball and socket ankle joint as so far described, limited cushioned flexion in various directions, and also limited movement about the vertical axis, is possible. But it is desirable to provide for relatively greater resistance to dorsiflexion, that is, upward movement of the fore-part of the foot, and also resistance to lateral or medial flexion, whilst permitting relatively less resistance to plantar flexion. To achieve this, a thick rubber buffer ring 11 is fitted over the shank 4A. The ring 11 has frustoconical inner and outer surfaces as shown. A depending skirt portion 12 of the lower socket part 5B engages the front portion of the buffer ring 11 at 12A. At each side of the shank 4A and ring 11 has the skirt portion extends rearwardly to provide in effect spaced side walls 12B, as shown in FIGS. 3 and 4 against which the buffer ring abuts when lateral or medial flexion occurs. The skirt portion is open at the back so that the rear surface of the ring 11 is free and remains uncompressed when plantar-flexion occurs. But when dorsi-flexion occurs the forward part of the ring 11 engages the rigid forward part of the skirt 12 at 12A, so that dorsi-flexion is resisted as the ring 11 is compressed. Lateral or medial flexion is also resisted by compression of the ring 11 as it engages a respective one of the rigid side walls 12B of the skirt portion 12. The degree of rotation about the vertical axis allowed by the ball and socket joint is substantially unaffected by the skirt portion 12 and buffer ring 11.

Variations are possible. For example, the rubber cover 6 could be omitted, the surfaces of the socket 5 being in sliding contact with the ball portion 4, or a one-piece socket could be used.

We claim:

1. An artificial leg comprising a shin member and a foot and, connecting the shin member and the foot, a ball and socket joint which includes a socket and a ball member, the ball member having a ball portion within the socket and a coupling shank, wherein (i) the socket includes an extension arranged to co-operate with an elastic buffer mounted between the coupling shank and the extension so as to provide resistance to dorsi-flexion of the foot relative to the shin member; (ii) the extension comprises a skirt shaped to engage a portion of the outer surface of the buffer; and (iii) the skirt subtends an angle of between 90° and 270° at a longitudinal axis of the coupling shank.

2. An artificial leg according to claim 1, wherein the elastic buffer comprises a ring encircling the coupling shank.

3. An artificial leg according to claim 1, wherein the skirt has a frusto-conical inner surface.

4. An artificial leg according to claim 2, wherein the ring has a frusto-conical outer surface which increases in diameter with increasing distance from the ball portion.

5. An artificial leg according to claim 1, wherein the foot is mounted on the ball and socket joint in such manner that the angular position of the foot may be adjusted about a generally medial-lateral axis relative to the combination of the socket and the ball member, and then fixed in the adjusted position.

6. An artificial leg according to claim 1, wherein the coupling shank connects the ball portion to the foot, and wherein the extension is disposed below the ball portion and in front of the shank.

7. An artificial leg according to claim 5, wherein the coupling shank has a convex part-cylindrical lower surface, and the foot has a corresponding part-cylindrical upwardly directed mating surface.

8. An artificial leg according to claim 7, wherein the said lower and upwardly directed surfaces are serrated to define a series of adjustment steps.

9. An artificial leg according to claim 7 wherein the curvatures of the said lower and upwardly directed surfaces are such that the foot is adjustable in position relative to the ball and socket joint about an axis situated above or passing through the centre of the ball and socket joint.

10. An artificial leg according to claim 6, wherein the socket comprises an upper portion and a lower portion which are clamped together to secure the ball portion in the socket with an elastic sleeve surrounding the ball portion, and wherein the extension is integral with the lower portion.

11. An artificial leg comprising:-
   a shin member;
   a foot;
   a ball and socket joint which includes
   a ball member attached to the foot and a socket member attached to the shin, the socket member having a downwardly extending anterior skirt portion; and
   an elastic buffer disposed below the joint between the skirt portion and the ball member for resisting dorsi-flexion of the foot relative to the shin member, the skirt portion subtending an angle of between 90° and 270° at a central vertical axis of the ball and socket joint.

12. An artificial leg according to claim 11, wherein the buffer comprises a ring encircling a downwardly extending coupling portion of the ball member, the skirt portion being shaped to engage an anterior portion of the outer surface of the ring.

13. An artificial limb component comprising a foot and a ball and socket ankle joint, the ankle joint including a ball member secured to the foot and a socket member for attachment to an upper limb component, wherein the socket member has a downwardly extending anterior skirt portion, and wherein an elastic buffer in the form of a ring is disposed between the skirt portion and the ball member for resisting dorsi-flexion of the foot relative to the upper limb component, the skirt portion subtending an angle of between 90° and 270° at a central vertical axis of the ball and socket joint.

* * * * *